(12) United States Patent
Yagi (10) Patent No.: US 10,413,156 B2
(45) Date of Patent: Sep. 17, 2019

(54) ENDOSCOPE DEVICE, ENDOSCOPIC SYSTEM, METHOD, AND COMPUTER-READABLE STORAGE DEVICE

(71) Applicant: OLYMPUS CORPORATION, Tokyo (JP)

(72) Inventor: Yukiyoshi Yagi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 15/686,950

(22) Filed: Aug. 25, 2017

(65) Prior Publication Data
US 2018/0177382 A1 Jun. 28, 2018

(30) Foreign Application Priority Data
Dec. 26, 2016 (JP) .................................. 2016-251713

(51) Int. Cl.
*H04N 5/232* (2006.01)
*H04N 5/225* (2006.01)
(Continued)

(52) U.S. Cl.
CPC ...... *A61B 1/00006* (2013.01); *A61B 1/00009* (2013.01); *A61B 1/00011* (2013.01); *A61B 1/00045* (2013.01); *A61B 1/05* (2013.01); *G06T 1/00* (2013.01); *G06T 1/20* (2013.01); *H04N 5/232* (2013.01); *H04N 5/23216* (2013.01); *H04N 5/23293* (2013.01); *H04N 5/22525* (2018.08); *H04N 5/44504* (2013.01); *H04N 2005/2255* (2013.01)

(58) Field of Classification Search
CPC ............ A61B 1/00006; A61B 1/00009; A61B 1/00045; A61B 1/05; A61B 1/00011; G06T 1/20; G06T 1/00; H04N 2005/2255; H04N 5/232; H04N 5/23293; H04N 5/22525; H04N 5/44504
See application file for complete search history.

(56) References Cited

U.S. PATENT DOCUMENTS

| 9,313,403 B2 | 4/2016 | Hamada | |
| 2007/0192565 A1* | 8/2007 | Hoshino | ............. G06F 15/7832 712/34 |

(Continued)

FOREIGN PATENT DOCUMENTS

JP 2015-41924 A 3/2015

*Primary Examiner* — Anner N Holder
(74) *Attorney, Agent, or Firm* — Scully, Scott, Murphy & Presser, P.C.

(57) ABSTRACT

An endoscopic device including: an image sensor configured to acquire image data; and a first processor comprising hardware, wherein the first processor is configured to: execute a first processing to process the image data, wherein the first processing involves a first processing load; acquire an instruction to perform a second processing to process the image data, wherein the second processing involves a second processing load different from the first processing load; and in response to acquiring the instruction, control a communication interface to output the image data to a second processor comprising hardware, wherein the second processor is provided separately from the endoscopic device, and wherein the second processor is configured to execute the second processing based on the image data.

18 Claims, 6 Drawing Sheets

(51) Int. Cl.
*H04N 5/445* (2011.01)
*A61B 1/00* (2006.01)
*A61B 1/05* (2006.01)
*G06T 1/20* (2006.01)
*G06T 1/00* (2006.01)

(56) References Cited

U.S. PATENT DOCUMENTS

| | | | | |
|---|---|---|---|---|
| 2007/0195164 A1* | 8/2007 | Fukuyama | ............. | H04N 7/183 348/65 |
| 2012/0062573 A1* | 3/2012 | Kashimoto | ............... | G06T 1/60 345/501 |
| 2015/0272429 A1* | 10/2015 | Shigeta | .................. | A61B 1/045 348/65 |

* cited by examiner

ENDOSCOPE DEVICE, ENDOSCOPIC SYSTEM, METHOD, AND COMPUTER-READABLE STORAGE DEVICE

CROSS-REFERENCE TO RELATED APPLICATIONS

This application claims priority based on Japanese Patent Application No. JP 2016-251713, filed on Dec. 26, 2016, the content of which is incorporated herein by reference.

BACKGROUND

Technical Field

The present invention relates to an endoscope device, an endoscope system, method and computer-readable storage device.

Background Art

Conventionally, there has been an endoscope system which records still images, which are obtained by causing moving images to be still. In some cases, the still images are subjected to image processing which is more advanced than the image processing for the moving images.

For example, JP 2015-41924 A discloses an image processing device which selects a reference image and a synthesis target image from a plurality of image groups having different image pickup time and synthesizes the synthesis target image with the reference image to generate image synthesis as image processing of a still image.

SUMMARY

An aspect of the preset invention is, an endoscopic device comprising: an image sensor configured to acquire image data; and a first processor comprising hardware, wherein the first processor is configured to: execute a first processing to process the image data, wherein the first processing involves a first processing load; acquire an instruction to perform a second processing to process the image data, wherein the second processing involves a second processing load different from the first processing load; and in response to acquiring the instruction, control a communication interface to output the image data to a second processor comprising hardware, wherein the second processor is provided separately from the endoscopic device, and wherein the second processor is configured to execute the second processing based on the image data.

Another aspect of the present invention is a system comprising: the endoscopic device; and the second processor.

Another aspect of the present invention is a method comprising: controlling an image sensor of an endoscopic device to capture image data; executing, by a first processor comprising hardware of the endoscopic device, a first processing to process the image data, wherein the first processing involves a first processing load; acquiring, by the first processor, an instruction to perform a second processing to process the image data, wherein the second processing involves a second processing load different from the first processing load; and in response to acquiring the instruction, controlling, by the first processor, a communication interface to output the image data to a second processor comprising hardware, wherein the second processor is provided separately from the endoscopic device, and wherein he second processor is configured to exe cute the second processing based on the image data.

Another aspect of the present invention is a computer-readable storage device storing instructions, wherein the instructions cause a first processor of an endoscopic device executing the instructions to perform, at least: controlling an image sensor of the endoscopic device to capture image data; executing a first processing to process the image data, wherein the first processing involves a first processing load; acquiring an instruction to perform a second processing to process the image data, wherein the second processing involves a second processing load different from the first processing load; and in response to acquiring the instruction, controlling a communication interface to output the image data to a second processor comprising hardware, wherein the second processor is provided separately from the endoscopic device, and wherein the second processor is configured to execute the second processing based on the image data.

DETAILED DESCRIPTION

Hereinafter, embodiments of the present invention will be described with reference to drawings.

(Configuration)

Figure 1:
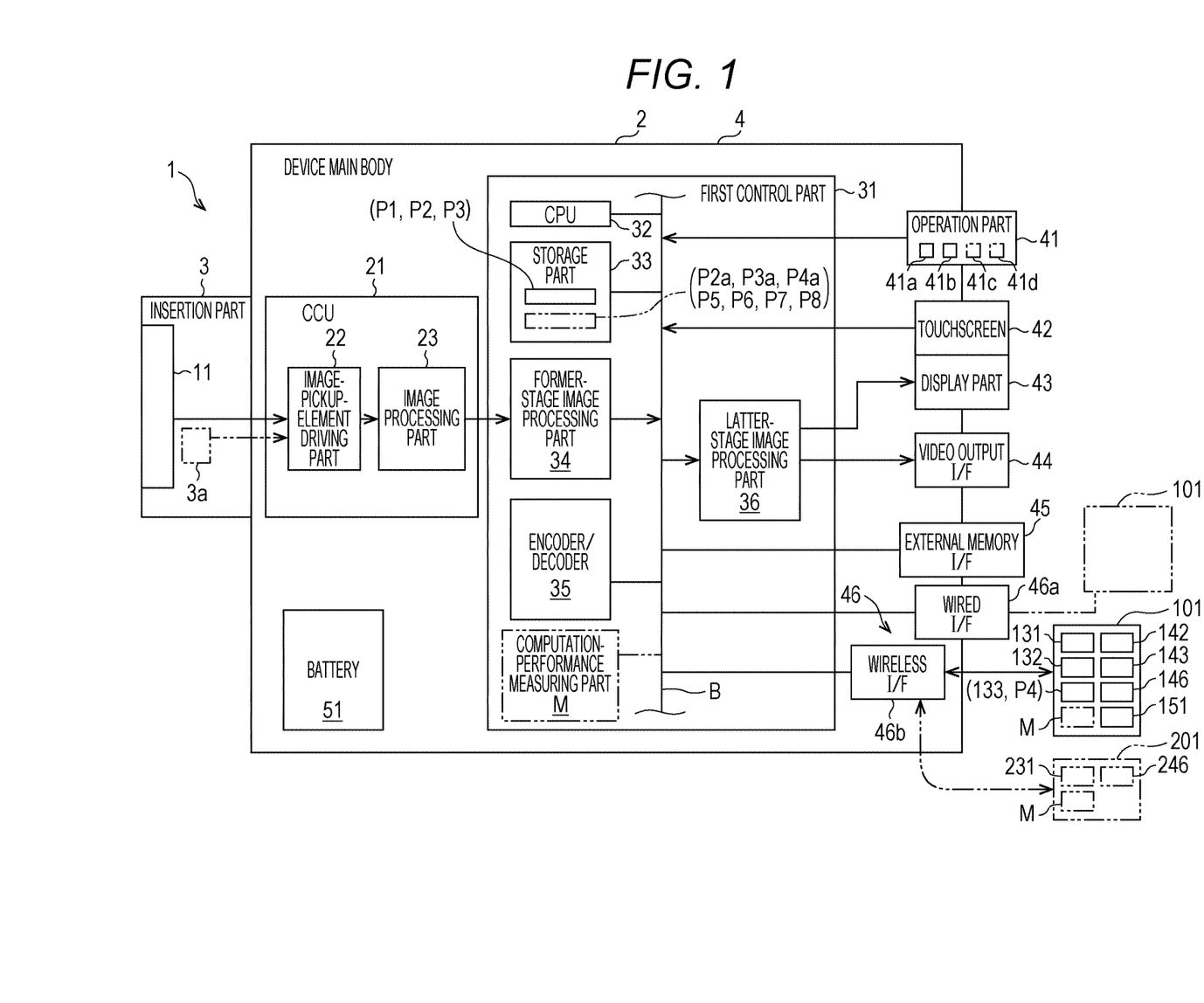
FIG. 1 is a block diagram showing a configuration example of an endoscope system according to an embodiment of the present invention.

FIG. 1 is a block diagram showing a configuration example of an endoscope system according to an embodiment of the present invention.

The endoscope system 1 has an endoscope device 2, which is a first processing device, and a second processing device 101, which is provided outside the endoscope device 2. The endoscope device 2 is connected to the second processing device 101.

The endoscope device 2 has an insertion part 3 and a device main body 4.

The insertion part 3 is formed in a slender shape so that the insertion part can be inserted into a subject, and the insertion part 3 is attached to the device main body 4. An image-pickup part 11 is provided at a distal end part of the insertion part 3. The image-pickup part 11 has a photoelectric conversion element such as a CCD. The image-pickup part 11 is connected to a CCU 21 of the device main body 4. The image-pickup part 11 picks up an image (s) of the subject under control of the CCU 21 and outputs an analog image-pickup signal (s) to the CCU 21. Note that the photoelectric conversion element is not limited to a CCD, but may be formed by a CMOS or the like.

Other than the image-pickup part 11, a curving part configured to curve the insertion part 3 and a lighting part configured to light up the subject, which are not shown are provided at the insertion part 3.

The device main body 4 has a CCU 21, a first control part 31, an operation part 41, a touchscreen 42, a first display part 43, a video output interface (hereinafter, abbreviated as "I/F") 44, an external memory I/F 45, a first communication part 46, and a first battery 51.

The CCU 21 is connected to the image-pickup part 11, carries out various control of the image-pickup part 11, generates endoscope images based on the image-pickup signals input from the image-pickup part 11, and outputs the endoscope images to the first control part 31. The CCU 21 has an image-pickup-element driving part 22 and an image processing part 23.

The image-pickup-element driving part 22 carries out driving of the image-pickup part 11, generates endoscope images based on the image-pickup signals input from the image-pickup part 11, and outputs the endoscope images to the image processing part 23.

The image processing part 23 generates endoscope images of an interlace method based on the image-pickup signals input from the image-pickup-element driving part 22, carries out image processing such as a noise reduction processing, a profile emphasizing processing, and contrast adjustment based on a single endoscope image, and outputs the endoscope image which has undergone the image processing to the first control part 31. Note that the image processing carried out by the image processing part 23 is not limited to the noise reduction processing, the profile emphasizing processing, and the contrast adjustment based on the single endoscope image, other image processing may be carried out, and/or part of the image processing may be carried out.

The first control part 31 carries out control of each part of the endoscope device 2. Moreover, the first control part 31 executes live-image display processing, which is first processing, based on the endoscope images input from the CCU 21 and causes the second processing device 101 to execute still-image output processing, which is second processing, in parallel. The first control part 31 has a central processing device (hereinafter, referred to as "CPU") 32, a storage part 33, a former-stage image processing part 34, an encoder/decoder 35, and a latter-stage image processing part 36. The CPU 32, the storage part 33, the former-stage image processing part 34, the encoder/decoder 35, and the latter-stage image processing part 36 are mutually connected via a bus B. Alternatively, on a one-to-one basis, the former-stage image processing part 34 is connected to the encoder/decoder 35, and the former-stage image processing part 34 is connected to the latter-stage image processing part 36.

The CPU 32 can read various programs stored in the storage part 33 and execute various processing. Functions of the first control part 31 are realized by executing the various programs.

The storage part 33 includes storage devices such as a work RAM, which is a volatile memory, and a non-volatile memory such as a flash memory (ROM). Other than the various programs and data for carrying out control of the endoscope device 2, the storage part 33 also stores programs of a normal-live-display processing part P1, a freeze processing part P2, and a recording processing part P3 and the endoscope images input from the former-stage image processing part 34 and the second processing device 101.

The former-stage image processing part 34 is a circuit which carries out former-stage image processing. The former-stage image processing part 34 converts the endoscope images of the interlace method input from the image processing part 23 to images of a progressive method and outputs the images to at least one of the storage part 33, the latter-stage image processing part 36, and the encoder/decoder 35. The endoscope images output from the former-stage image processing part 34 are, for example, 60 moving images per 1 second.

The encoder/decoder 35 is a circuit which compresses and decompresses the endoscope images. The encoder/decoder 35 compresses the endoscope images, which are input from the former-stage image processing part 34 or the storage part 33, and outputs the images to at least one of the external memory I/F 45 and the first communication part 46. Moreover, the encoder/decoder 35 can also decompress various information input from the external memory I/F 45 and the first communication part 46.

The latter-stage image processing part 36 is a circuit which carries out scaling processing to adjust the sizes of images and OSD processing to superimpose predetermined characters on images. The latter-stage image processing part 36 is connected to the first display part 43 and the video output I/F 44. The latter-stage image processing part 36 subjects the endoscope images, which are input from the storage part 33 or the former-stage image processing part 34, to scaling processing and OSD processing and outputs the images to at least one of the first display part 43 and the video output I/F 44.

The operation part 41 is configured so that various instructions can be input to the endoscope device 2. The operation part 41 is connected to the first control part 31. If there is an instruction input, the operation part 41 outputs a control signal corresponding to the instruction input to the first control part 31. The operation part 41 has a freeze-instruction input part 41a for inputting a freeze instruction of the endoscope image and canceling the freeze instruction and a recording-instruction input part 41b for inputting a recording instruction of the endoscope image. The freeze-instruction input part 41a has, for example, an operation button with which the freeze instruction is input by pressing the button once, and the freeze instruction is canceled by pressing the button once more. The recording-instruction input part 41b has an operation button(s), and, for example, a recording instruction is input by pressing the button. Note that the operation part 41 may have a menu button(s) and other operation buttons, which are not shown.

The touchscreen 42 is disposed to be superimposed on the first display part 43 and is configured so that various instructions can be input to the endoscope device 2. The touchscreen 42 is connected to the first control part 31. If there is an instruction input, the touchscreen 42 outputs a control signal corresponding to the instruction input to the first control part 31.

The first display part 43 includes a display device such as a liquid crystal panel. The first display part 43 displays the endoscope images input from the latter-stage image processing part 36.

The video output I/F 44 is a circuit which connects an unshown external monitor via a cable.

The external memory I/F 45 is a circuit which connects an unshown memory card. The external memory I/F 45 is connected to the first control part 31.

Figure 2:
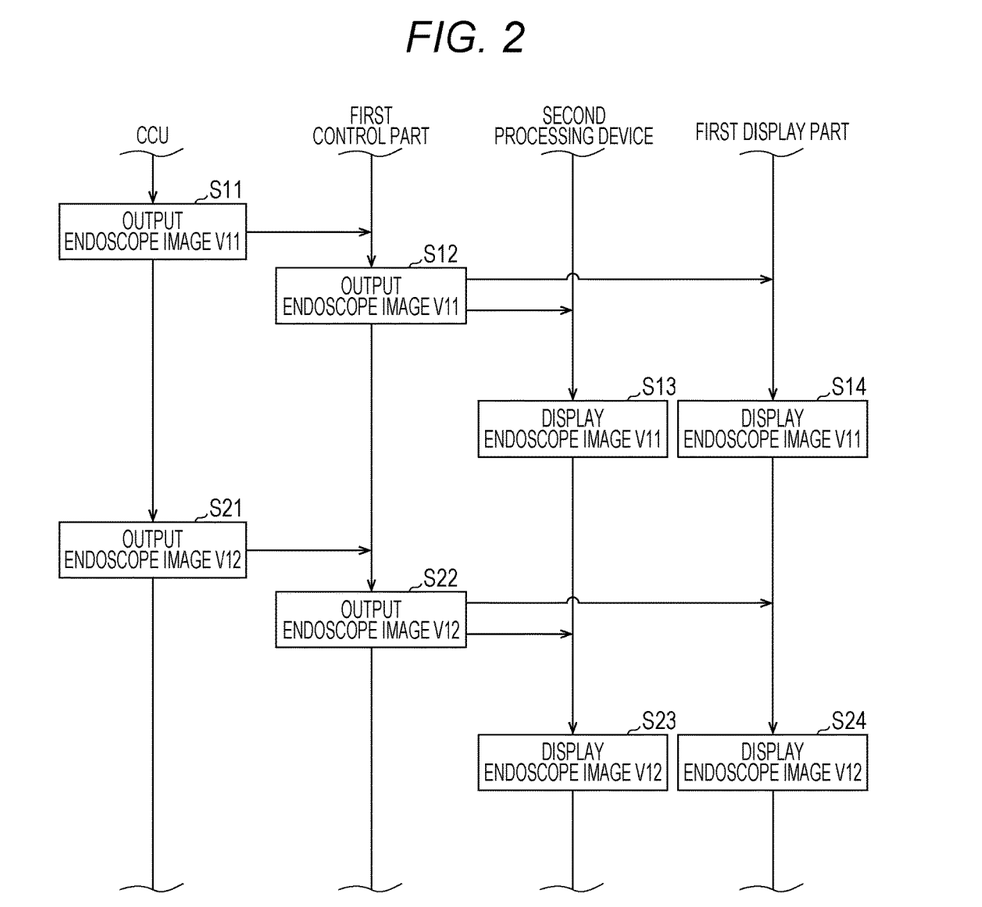
FIG. 2 is a flow chart showing a flow of normal-live-display processing of the endoscope system according to the embodiment of the present invention.

The first communication part 46 is a circuit which carries out communication with an external device(s). The first communication part 46 is connected to the first control part 31. The first communication part 46 has a wired I/F 46a, which communicates with the external device(s) by wired communication, and a wireless I/F 46b, which communicates with the external device(s) by wireless communication. In FIG. 2, the wireless I/F 46b is connected to the second processing device 101.

The first battery 51 can supply a power source to each part of the endoscope device 2.

The second processing device 101 can execute various processing in accordance with the instructions of the endoscope device 2. The second processing device 101 is, for example, a portable information terminal device. The second processing device 101 has a second control part 131, a second touchscreen 142, a second display part 143, a second communication part 146, and a second battery 151.

The second control part 131 has a CPU 132 and a memory 133 and can execute various programs stored in the memory 133. In the memory 133, a program of an image-quality improvement processing part P4 for improving the image quality of still images is stored.

Image-quality improvement processing of the image-quality improvement processing part P4 is noise reduction processing based on a plurality of endoscope images. In the noise reduction processing based on the plurality of endoscope images, for example, noise is reduced by aligning the positions of the endoscope images based on the plurality of endoscope images and carrying out weighted averaging of pixel values in the mutually overlapped regions of the endoscope images.

The second touchscreen 142 is disposed to be superimposed on the second display part 143 and is configured so that various instructions can be input to the second processing device 101.

The second display part 143 includes a display device such as a liquid crystal panel. The second display part 143 is connected to the second control part 131 and displays various images under the control of the second control part 131.

The second communication part 146 is a circuit which carries out communication with the endoscope device 2.

The second battery 151 can supply a power source to each part of the second processing device 101.

By virtue of this, in normal-live-display processing and recording processing, the first control part 31 of the endoscope device 2 executes display processing of live images by the former-stage image processing part 34 and the latter-stage image processing part 36 based on the endoscope images input from the image-pickup part 11 and displays the live images by the first display part 43.

Moreover, in freeze processing, the first control part 31 stores the endoscope images, which have undergone image processing by the former-stage image processing part 34, in the storage part 33.

Moreover, in the recording processing, the first control part 31 generates, by the encoder/decoder 35, parallel processing information for carrying out parallel processing in the second processing device 101 based on the endoscope images stored in the storage part 33 and outputs the generated parallel processing information to the second processing device 101 via the first communication part 46.

The second control part 131 of the second processing device 101 executes image-quality improvement processing based on the parallel processing information input via the second communication part 146 and outputs the image-quality-improved still images to the endoscope device 2.

Thus, the endoscope device 2, which is the first processing device, has the first communication part 46, which carries out communication with the second processing device 101, and the first control part 31, which executes first processing to output first information, outputs the parallel processing information for carrying out parallel processing to the second processing device 101 via the first communication part 46, and carries out control of second processing, which is executed in the second processing device 101 in parallel with the first processing. The second processing device 101 has the second communication part 146, which carries out communication with the endoscope device 2, and the second control part 131, which executes second processing to output second information in parallel with the first processing based on the parallel processing information input via the second communication part 146. Moreover, the second processing device 101 outputs the second information to the endoscope device 2 via the second communication part 146.

Specifically, the endoscope device 2 has the image-pickup part 11, which picks up images of a subject and outputs endoscope images; the first control part 31 executes the first processing based on the endoscope image, outputs first image information, and outputs the endoscope image to the second processing device 101; and the second control part 131 executes the second processing and outputs second image information, which is a still image. The endoscope device has the display part and the storage part, the display part displays the first image information, the storage part can store the endoscope image, and the first control part outputs the endoscope image, which is stored in the storage part, to the second processing device 101.

In the present embodiment, the first processing is display processing of a live image. The first information output by executing the first processing is the first image information and is, more specifically, a live image.

Meanwhile, the second processing is image-quality improvement processing of a still image. The second information output by executing the second processing is the second image information and is, more specifically, an image-quality-improved still image.

(Operation)

(Normal-Live-Display Processing)

Subsequently, operations of the endoscope system 1 will be described.

First, a flow of normal-live-display processing will be described.

FIG. 2 is a flow chart showing the flow of the normal-live-display processing of the endoscope system 1 according to the embodiment of the present invention.

When the insertion part 3 is inserted into a subject and starts observing the subject, image-pickup signals are input from the image-pickup part 11 to the CCU 21. The CCU 21 generates an endoscope image based on the image-pickup signals.

The CCU 21 outputs the endoscope image V11 (S11). The CCU 21 outputs the endoscope image V11 to the first control part 31.

The first control part 31 outputs the endoscope image V11 (S12). The first control part 31 subjects the endoscope image V11, which is input from the CCU 21 in S11, to image processing by the former-stage image processing part 34. The first control part 31 compresses the endoscope image V11, which has undergone the image processing, by the encoder/decoder 35 and outputs it to the second processing device 101 as parallel processing information via the first communication part 46. Moreover, the first control part 31 further subjects the endoscope image V11, which has undergone the image processing, to image processing by the latter-stage image processing part 36 and outputs the image to the first display part 43.

The second processing device 101 displays the endoscope image V11 (S13). The second control part 131 causes the second display part 143 to display the endoscope image V11, which is input from the endoscope device 2.

The first display part 43 displays the endoscope image V11 (S14). The first display part 43 displays the endoscope image V11, which is input from the first control part 31.

In S21 to S24, the processing same as S11 to S14 is carried out based on an endoscope image V12.

Until a freeze instruction is input, the processing of S11 to S14 is repeated for sequentially input endoscope images.

The processing of repeating S11 to S14 constitutes the normal-live-display processing of the normal-live-display processing part P1 according to the embodiment.

(Freeze Processing)

Next, a flow of freeze processing will be described.

Figure 3:
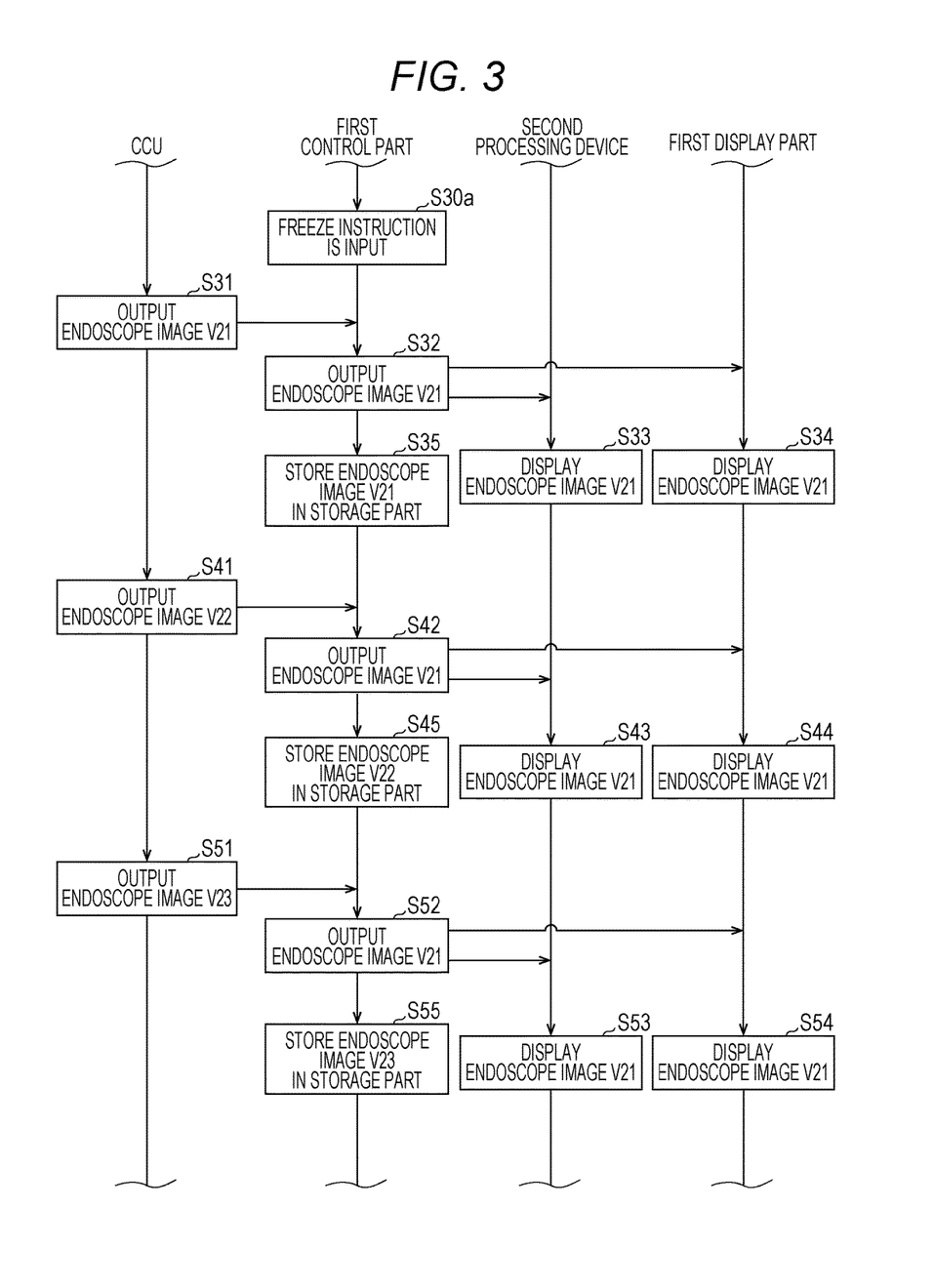
FIG. 3 is a flowchart showing a flow of freeze processing of the endoscope system according to the embodiment of the present invention.

FIG. 3 is a flow chart showing the flow of the freeze processing of the endoscope system 1 according to the embodiment of the present invention.

In the freeze processing, a still image is displayed by the first display part 43 and the second display part 143 so that the endoscope image in a still state can be checked by a user(s).

A freeze instruction is input (S30a). When the freeze instruction is input by the freeze-instruction input part 41a, the first control part 31 starts the freeze processing.

The CCU 21 outputs an endoscope image V21 to the first control part 31 (S31), the first control part 31 outputs the endoscope image V21 to the first display part 43 and the second processing device 101 (S32), and the first display part 43 and the second processing device 101 display the endoscope image V21 (S33, S34).

The endoscope image V21 is stored in the storage part 33 (S35). The first control part 31 stores the endoscope image V21, which has undergone image processing by the former-stage image processing part 34 in S32, in the storage part 33.

In S41 to S45, the same processing as S31 to S35 is carried out, wherein the endoscope image V21 is displayed by the first display part 43 and the second display part 143, and the endoscope image V22 is stored in the storage part 33.

In S51 to S55, the same processing as S31 to S35 is carried out, wherein the endoscope image V21 is displayed by the first display part 43 and the second display part 143, and an endoscope image V23 is stored in the storage part 33.

Until a freeze canceling instruction is input or a recording instruction is input, the processing of S31 to S35 is repeated. If the freeze canceling instruction is input, the processing returns to the normal-live-display processing. Meanwhile, if the recording instruction is input, the processing proceeds to recording processing.

The processing of repeating S31 to S35 constitutes the freeze processing of the freeze processing part P2 according to the embodiment.

Note that, if the capacity of the storage part 33 is insufficient due to storing of endoscope images, the older endoscope images thereof are deleted.

(Recording Processing)

Figure 4:
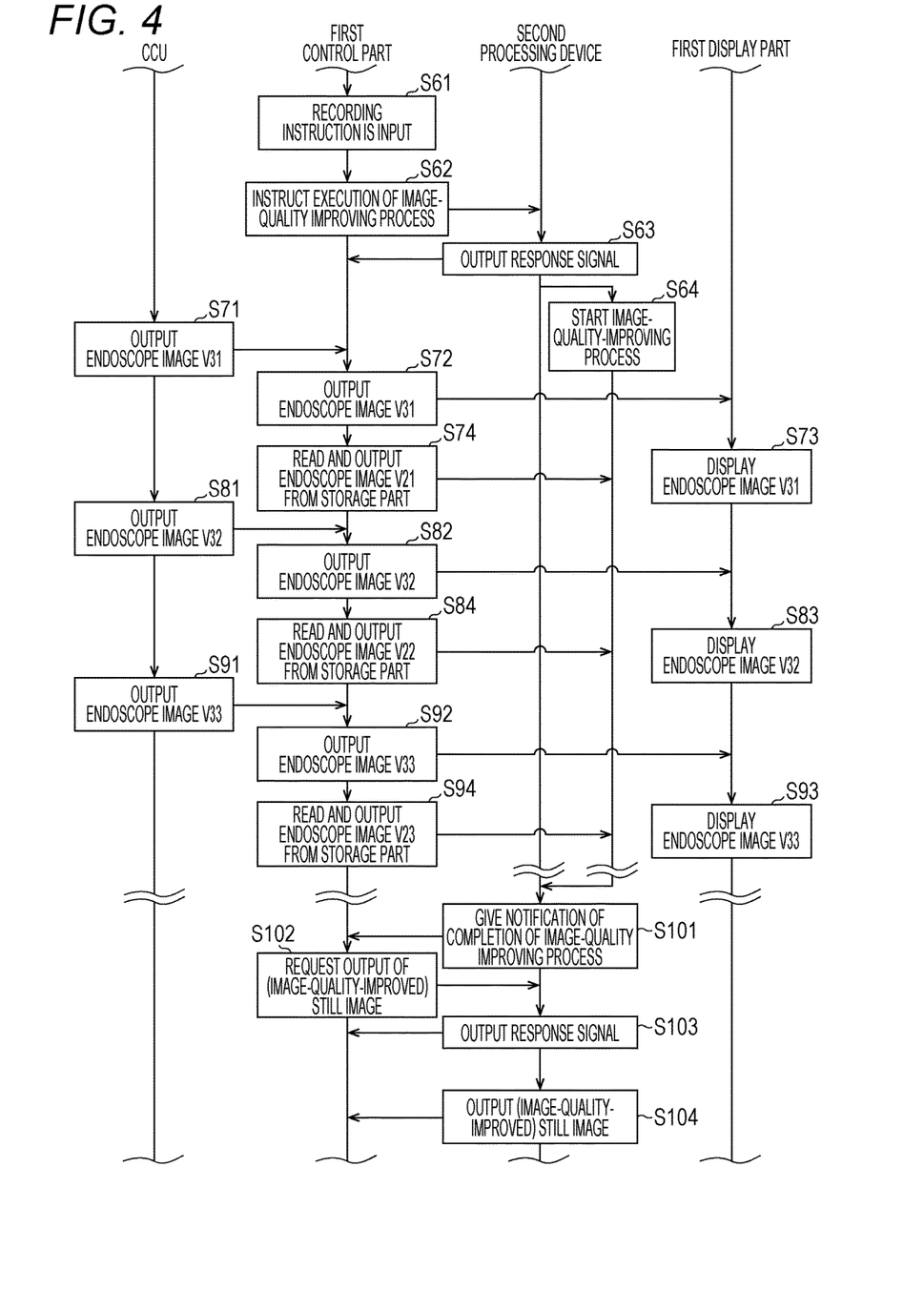
FIG. 4 is a flow chart showing a flow of recording processing of the endoscope system according to the embodiment of the present invention.

Next, a flow of recording processing will be described.
FIG. 4 is a flow chart showing the flow of the recording processing of the endoscope system 1 according to the embodiment of the present invention.

In the recording processing, the endoscope device 2 displays live images so that the user(s) can observe the live images, and the second processing device 101 is caused to carry out image-quality improvement processing of still images so that the live images are not stagnated.

A recording instruction is input (S61). When the recording instruction is input by the recording-instruction input part 41b, the first control part 31 starts the recording processing.

The first control part 31 instructs execution of image-quality improvement processing (S62). The first control part 31 outputs parallel processing information to the second processing device 101 via the first communication part 46 and instructs the second processing device 101 to execute the image-quality improvement processing.

The second processing device 101 outputs a response signal (S63). When the parallel processing information is input in S62, the second control part 131 outputs the response signal to the endoscope device 2 via the second communication part 146.

The second processing device 101 starts the image-quality improvement processing (S64). The program of the image-quality improvement processing part P4 is read from the memory 133, and the second control part 131 starts the image-quality improvement processing of still images.

The CCU 21 outputs an endoscope image V31 (S71). The CCU 21 outputs the endoscope image V31 to the first control part 31.

The first control part 31 outputs the endoscope image V31 (S72). When the endoscope image V31 is input from the CCU 21 in S71, the first control part 31 carries out image processing by the former-stage image processing part 34. The first control part 31 further subjects the endoscope image V31, which has undergone the image processing, to image processing by the latter-stage image processing part 36 and outputs the image to the first display part 43.

The first display part 43 displays the endoscope image V31 (S73). The first display part 43 displays the endoscope image V31, which is input from the first control part 31.

The first control part 31 reads and outputs the endoscope image V21 from the storage part 33 (S74). The first control part 31 reads the endoscope image, which is stored in the storage part 33 in S35, compresses the image by the encoder/decoder 35 to generate parallel processing information, and outputs the information to the second processing device 101.

In S81 to S84, the processing same as S71 to S74 is carried out, wherein the endoscope image V32 is displayed by the first display part 43, and the endoscope image V22, which is stored in the storage part 33 in S45, is output to the second processing device 101.

In S91 to S94, the processing same as S71 to S74 is carried out, wherein the endoscope image V33 is displayed by the first display part 43, and the endoscope image V23, which is stored in the storage part 33 in S55, is output to the second processing device 101.

Until the first control part 31 is notified of completion of the image-quality improvement processing, the processing of S71 to S74 is repeated.

The second processing device 101 gives a notification of the completion of the image-quality improvement processing (S101). When the image-quality improvement processing is completed, the second control part 131 gives the notification of the completion of the image-quality improvement processing to the first control part 31 via the second communication part 146.

The first control part 31 requests the second processing device 101 to output the still images which have undergone the image-quality improvement processing (S102).

The second processing device 101 outputs a response signal to the endoscope device 2 (S103).

The second processing device 101 outputs the still images, which have undergone the image-quality improvement processing, to the endoscope device 2 (S104).

When the still images are input, the endoscope device 2 stores the still images in the storage part 33 and starts normal-live-display processing.

The processing from S61 to S104 constitutes the recording processing of the recording processing part P3 according to the embodiment.

Thus, in the present embodiment, in response to the instruction input of the recording-instruction input part 41*b*, the first control part 31 outputs the endoscope images, which are stored in the storage part 33, to the second processing device 101.

In a processing method of the endoscope system 1, the endoscope device 2, which is the first processing device having the first control part 31, and the second processing device 101, which is provided outside the endoscope device 2 and has the second control part 131, are prepared; the first processing is executed by the first control part 31 to output the first information, the parallel processing information for carrying out parallel processing is output to the second processing device 101 by the first control part 31, and the second processing is executed by the second control part 131 in parallel with the first processing based on the input parallel processing information to output the second information.

According to the above described embodiment, even if high-load freeze processing temporarily occurs, the endoscope system 1 can suppress stagnation of the processing of the live image display.

Moreover, in the image processing such as image-quality improvement processing which comparatively takes computation time, computation processing is executed in the side of the second processing device 101. As a result, even immediately after image-pickup of still images, operability of the operation part 41 and the touchscreen 42 and display quality of the first display part 43 are not deteriorated, and usability and inspection efficiency are improved.

Moreover, even in the image processing which comparatively takes computation time, processing resources of the second processing device 101 are preferentially used to carry out image processing to reduce the processing load of the endoscope device 2, which displays live images, and usability and inspection efficiency are improved without deteriorating the display quality of the live images.

(Modification Example 1 of Embodiment)

In the embodiment, the image-quality improvement processing is carried out in accordance with the input of the recording instruction, but may be carried out in accordance with input of freeze processing.

Figure 5:
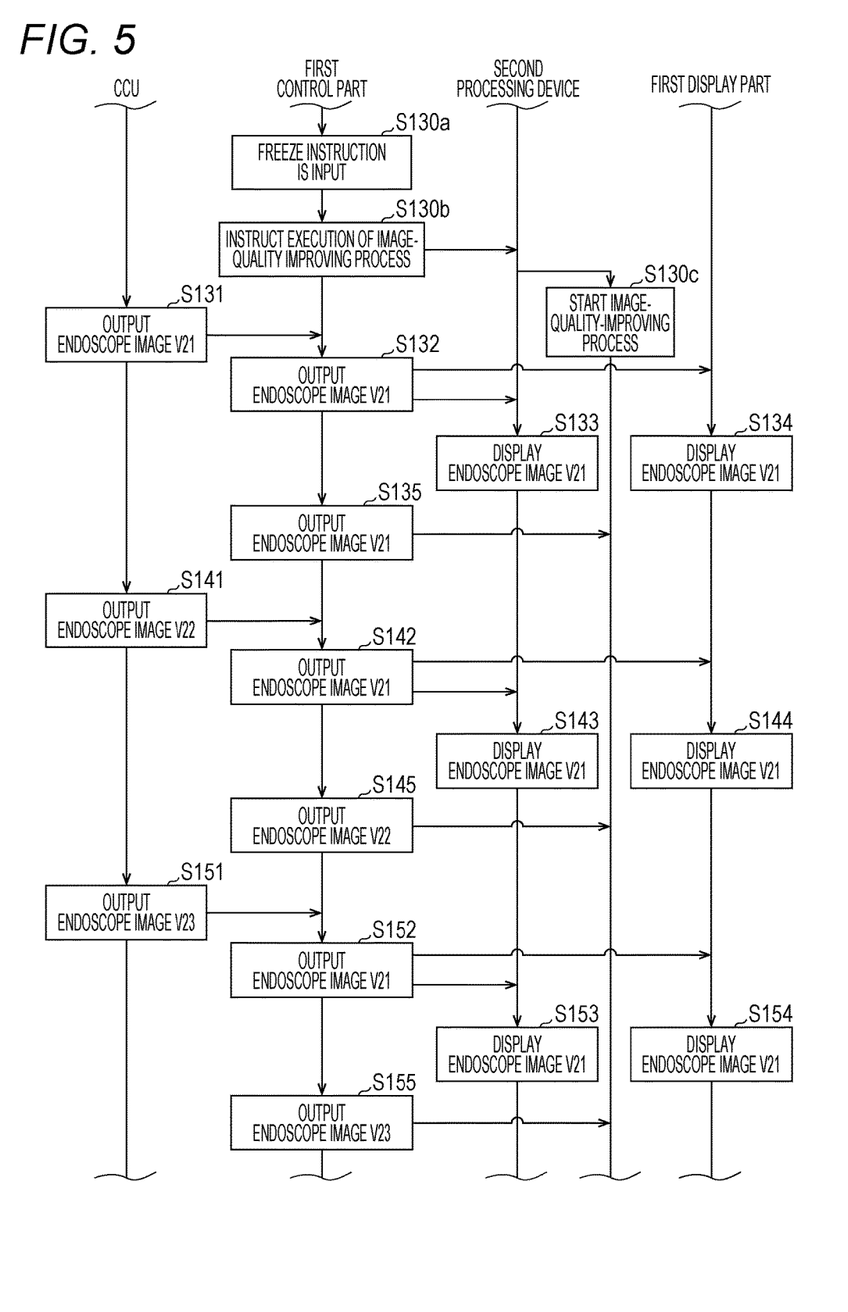
FIG. 5 is a flowchart showing a flow of freeze processing of the endoscope system according to Modification Example 1 of the embodiment of the present invention.

FIG. 5 is a flow chart showing a flow of the freeze processing of the endoscope system 1 according to Modification Example 1 of the embodiment of the present invention. In the description of the present modification example, the configurations same as the embodiment and other modification examples will be denoted by the same reference signs, and the description thereof will be omitted. Note that, similarly in Modification Examples 2 to 12, the configurations same as the embodiment and other modification examples will be denoted by the same reference signs, and the description thereof will be omitted.

In the storage part 33, programs of a freeze processing part P2*a* and a recording processing part P3*a* according to the present modification example are stored.

Next, the flow of the freeze processing according to Modification Example 1 will be described.

A freeze instruction is input (S130*a*).

The first control part 31 instructs the second processing device 101 to execute image-quality improvement processing (S130*b*).

The second processing device 101 starts the image-quality improvement processing (S130*c*). S130*c* is the same as S64.

S131 to S134 are the same as S31 to S34.

The first control part 31 outputs the endoscope image V21 (S135). The first control part 31 outputs the endoscope image V21 to the second processing device 101.

In S141 to S145, the same processing as S131 to S135 is carried out, wherein the endoscope image V21 is displayed by the first display part 43 and the second display part 143, and the endoscope image V22 is output to the second processing device 101.

In S151 to S155, the same processing as S131 to S135 is carried out, wherein the endoscope image V21 is displayed by the first display part 43 and the second display part 143, and the endoscope image V23 is output to the second processing device 101.

Until a freeze canceling instruction is input or a recording instruction is input, the processing of S131 to S135 is repeated. If the freeze canceling instruction is input, the processing returns to the normal-live-display processing. Meanwhile, if the recording instruction is input, the processing proceeds to recording processing.

The processing of repeating S131 to S135 constitutes the freeze processing of the freeze processing part P2*a* according to Modification Example 1 of the embodiment.

Thus, in Modification Example 1, in response to the instruction input of the freeze-instruction input part 41*a*, the endoscope device 2 outputs the endoscope images, which are stored in the storage part 33, to the second processing device 101. Moreover, in the second processing device 101, the image-quality improvement processing is started.

Figure 6:
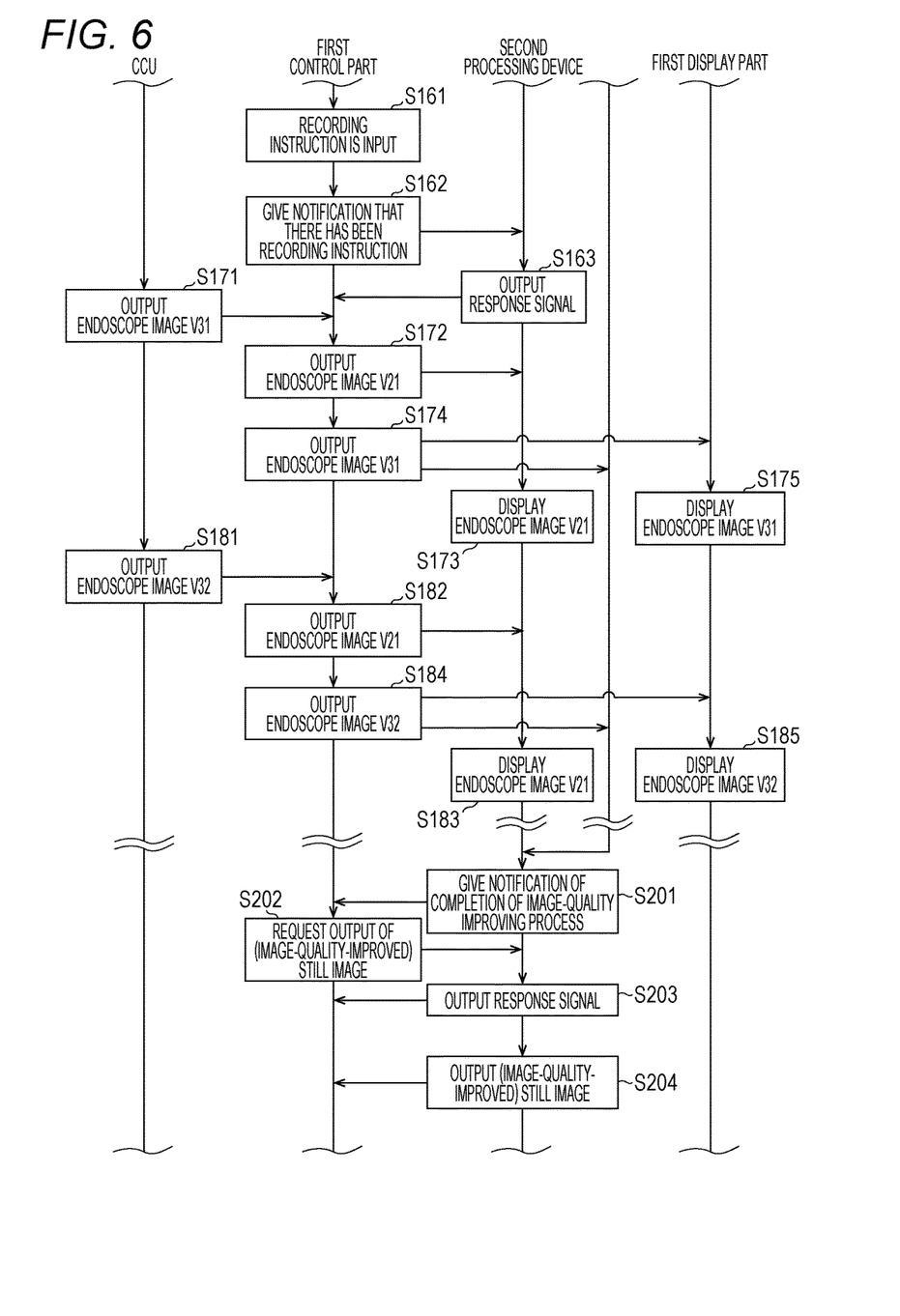
FIG. 6 is a flow chart showing a flow of recording processing of the endoscope system according to Modification Example 1 of the embodiment of the present invention.

Next, the flow of the recording processing according to Modification Example 1 will be described.

FIG. 6 is a flow chart showing the flow of the recording processing of the endoscope system 1 according to Modification Example 1 of the embodiment of the present invention.

A recording instruction is input (S161).

The first control part 31 gives a notification to the second processing device 101 that there has been the recording instruction (S162).

The second processing device 101 outputs a response signal to the endoscope device 2 (S163).

The CCU 21 outputs the endoscope image V31 to the first control part 31 (S171).

The first control part 31 outputs the endoscope image V21 to the second processing device 101 (S172).

The second processing device 101 displays the endoscope image V21 (S173).

The first control part 31 outputs the endoscope image V31 (S174). The first control part 31 subjects the endoscope image V31, which is input from the CCU 21 in S171, to image processing by the former-stage image processing part 34. The first control part 31 compresses the endoscope image V31, which has undergone the image processing by the former-stage image processing part 34, by the encoder/decoder 35 to generate parallel processing information and outputs the information to the second processing device 101. Moreover, the first control part 31 further subjects the endoscope image V31, which has undergone the image processing, to image processing by the latter-stage image processing part 36 and outputs the image to the first display part 43.

The first display part 43 displays the endoscope image V31 (S175).

In S181 to S185, by the same processing as S171 to S175, the endoscope image V32 is displayed by the first display part 43, and the endoscope image V21 is displayed by the second display part 143. Moreover, the endoscope image V32 is output to the second processing device 101.

Since the processing of S201 to S204 is the same as S101 to S104, description thereof will be omitted.

The processing from S161 to S204 constitutes the recording processing of the recording processing part P3a according to Modification Example 1 of the embodiment.

By virtue of this, in the endoscope system 1, after there is the freeze instruction, the image-quality improvement processing of the second processing device 101 is executed without waiting a recording instruction, and completion of the image-quality improvement processing can be speeded up.

(Modification Example 2 of Embodiment)

In the embodiment, the image-quality improvement processing is executed by the second processing device 101, but may be executed by the endoscope device 2.

Thus, in the present modification example, first processing is image-quality improvement processing of still images, and second processing is display processing of live images.

In Modification Example 2, the storage part 33 has an image-quality improvement processing part P4a.

In Modification Example 2, in normal-live-display processing and recording processing, the first control part 31 of the endoscope device 2 generates parallel processing information by the former-stage image processing part 34 and the encoder/decoder 35 based on the endoscope image input from the image-pickup part 11, outputs the information to the second processing device 101, and causes the second display part 143 to display live images.

Moreover, in freeze processing, based on endoscope images input from the image-pickup part 11, the first control part 31 stores the endoscope images, which have undergone image processing by the former-stage image processing part 34, in the storage part 33.

Moreover, in recording processing, based on the endoscope images stored in the storage part 33, the first control part 31 executes image-quality improvement processing by the image-quality improvement processing part P4a to generate image-quality-improved still images.

(Modification Example 3 of Embodiment)

In Modification Example 2 of the embodiment, the first control part 31 waits for the recording instruction to execute the image-quality improvement processing by the image-quality improvement processing part P4a. However, like Modification Example 1 of the embodiment, after there is the freeze processing, the image-quality improvement processing may be executed without waiting for the recording instruction.

(Modification Example 4 of Embodiment)

In Modification Example 1 of the embodiment, the endoscope device 2 carries out the display processing of the live images, and the second processing device 101 carries out the image-quality improvement processing of the still images. In Modification Example 2 and Modification Example 3, the endoscope device 2 carries out the image-quality improvement processing of the still images, and the second processing device 101 carries out the display processing of the live images. However, a determination processing part P5 may determine which devices are to respectively carry out the display processing of the live images and the image-quality improvement processing of the still images from among the endoscope device 2 and the second processing device 101.

In Modification Example 4, the first control part 31 has the determination processing part P5, which carries out determination processing for determining which devices are to respectively carry out the display processing of the live images and the image-quality improvement processing of the still images from among the endoscope device 2 and the second processing device 101.

In the storage part 33, priority information of each of the endoscope device 2 and the second processing device 101 is stored.

The endoscope device 2 has a priority-instruction input part 41c (2-dot chain line of FIG. 1), and the priority information is set in accordance with the instruction input of the priority-instruction input part 41c.

Based on the priority information, the determination processing part P5 determines the device to execute the display processing of the live images and the device to execute the image-quality improvement processing of the freeze processing by determination processing.

(Modification Example 5 of Embodiment)

In Modification Example 4 of the embodiment, the priority information is set in accordance with the instruction input of the priority-instruction input part 41c, but may be set by a priority setting part P6.

The priority setting part P6 may set the priority information, for example, in accordance with a terminal which has been finally operated by a user, may set the priority information in accordance with the usage frequency of each of the endoscope device 2 and the second processing device 101, may set the priority information in accordance with measurement results of computation-performance measuring parts M respectively provided in the endoscope device 2 and the second processing device 101, or may set the priority information in accordance with remaining battery levels of the first battery 51 and the second battery 151.

(Modification Example 6 of Embodiment)

In the embodiment and the modification examples, a processing-volume setting part P7 is not provided, but the processing-volume setting part P7 may be provided.

In Modification Example 6, the first control part 31 has the processing-volume setting part P7, which sets the processing volume of each of the first processing and the second processing. The first control part 31 outputs the parallel processing information of a volume corresponding to the processing volume to the second processing device 101.

The endoscope device 2 has a processing-volume-instruction input part 41d for inputting instructions of the processing volumes, and the processing volumes are set depending on the input of the instructions of the processing-volume-instruction input part 41d.

Note that the processing volumes may be set in accordance with the measurement results of the computation-performance measuring part M output to the processing-volume setting part P7 or may be set in accordance with the remaining battery levels of the first battery 51 and the second battery 151.

(Modification Example 7 of Embodiment)

In the embodiment and the modification examples, the endoscope system 1 has the endoscope device 2 and the second processing device 101, but may have a third processing device 201.

In Modification Example 7, the endoscope system. 1 has the third processing device 201. The third processing device 201 is provided outside the endoscope device 2 and the second processing device 101.

The endoscope device 2 has the first communication part 46, which carries out communication with the third processing device 201, and the first control part 31, which outputs parallel processing information for carrying out parallel processing to the third processing device 201 via the first communication part 46 and carries out control of third processing executed in the third processing device 201 in parallel with the first processing.

The third processing device 201 has a third communication part 246, which carries out communication with the endoscope device 2, and a third control part 231, which executes the third processing in parallel with the first processing based on the parallel processing information input via the third communication part 246 and outputs third information.

By virtue of this, in a case in which a plurality of portable information terminal devices are connected to the endoscope device 2 to carry out inspection, processing time can be shortened by dispersing computation processing to the endoscope device 2 and the plurality of portable information terminal devices even in the image processing which comparatively takes computation time, live properties of live images are ensured, in addition, image stopped periods of the processing device in which live images are not displayed are shortened, and usability and inspection efficiency are improved.

Note that, in Modification Example 7, the endoscope system 1 has the endoscope device 2, the second processing device 101, and the third processing device 201, but may further have a different processing device(s).

(Modification Example 8 of Embodiment)

In Modification Example 4, the determination processing part P5 determines the device to carry out the display processing of the live images and the device to carry out the image-quality improvement processing of the still images from among the endoscope device 2 and the second processing device 101. However, like Modification Example 7, the third processing device 201 may be provided, and the devices may be determined from among the endoscope device 2, the second processing device 101, and the third processing device 201.

The first control part 31 outputs the parallel processing information to the second processing device 101 and the third processing device 201. The parallel processing information, for example, may be live images divided by ODD/EVEN fields, may be the live images divided by color information (RGB, YCbCr), may be the live images divided by frame units, or may be the live images divided by display areas.

(Modification Example 9 of Embodiment)

In Modification Example 6, the processing-volume setting part P7 sets the processing volume of each of the first processing and the second processing. However, the third processing device 201 which carries out the third processing may be provided like Modification Example 7, and the processing volume of each of the first processing, the second processing, and the third processing may be set.

In Modification Example 9, the processing-volume setting part P7 sets the processing volume of each of the first processing, the second processing, and the third processing.

The first control part 31 outputs the parallel processing information having the volumes corresponding to processing volumes to the second processing device 101 and the third processing device 201 to instruct execution of the second processing and the third processing and synthesizes the second information, which is input from the second processing device 101, with the third information, which is input from the third processing device 201, to generate synthesis information.

(Modification Example 10 of Embodiment)

In the embodiment and the modification examples, a division processing part P8 is not provided, but the division processing part P8 may be provided.

The first control part 31 has the division processing part P8, which subjects the parallel processing information to division processing by a predetermined division method and division rate. The first control part 31 outputs the parallel processing information, which is divided by the division processing part P8, to the second processing device 101 and the third processing device 201 to instruct execution of the second processing and the third processing and synthesizes the second information, which is input from the second processing device 101, with the third information, which is input from the third processing device 201, to generate synthesis information.

The division rate may be set in accordance with the measurement results of the computation-performance measuring part M output to the division processing part P8 or may be set in accordance with the remaining battery levels of the first battery 51 and the second battery 151.

(Modification Example 11 of Embodiment)

In the embodiment and the modification examples, the second processing device 101 is connected to the wireless I/F 46b, but may be connected to the wired I/F 46a by a cable (2-dot chain line of FIG. 1).

(Modification Example 12 of Embodiment)

In the embodiment and the modification examples, the first processing, the second processing, and the third processing are image processing, but may be information processing other than image processing.

The endoscope device 2 of Modification Example 12 has a temperature sensor 3a at the distal end part of the insertion part 3. The temperature sensor 3a is connected to the CCU 21. The temperature sensor 3a measures the temperature in the subject and outputs the temperature to the CCU 21. The CCU 21 outputs endoscope images, which include the temperature information input from the temperature sensor 3a, to the former-stage image processing part 34. In the second processing device 101, the temperature in the subject is analyzed by the second processing, and, for example, if the temperature in the subject is high, image-quality improvement processing such as increasing red components of still images is carried out.

Note that, in Modification Example 12, the temperature sensor 3a is provided at the distal end part of the insertion part 3. However, for example, a different sensor(s) such as an acceleration sensor may be provided, and the endoscope images including the measurement information by the other sensor may be output and subjected to information processing by the second processing device 101.

Note that the noise reduction processing based on the plurality of endoscope images in the embodiment and the modification examples is an example of the image-quality improvement processing, and the image-quality improvement processing may be image-quality improvement processing by a different method.

Note that, in the embodiment and the modification examples, the processing carried out in parallel with the display processing of the live images is the image-quality improvement processing of the still images. However, the image-quality improvement processing is an example, and the processing may be different image processing.

Note that, in the embodiment and the modification examples, the endoscope images subjected to the image processing by the former-stage image processing part 34 are directly output to the second processing device 101. However, the endoscope images subjected to the image processing by the former-stage image processing part 34 may be stored in the storage part 33, and the endoscope images may be output from the storage part 33 to the second processing device 101.

Each "part" in the present description is an idea corresponding to each function of the embodiment and is not necessarily corresponding to particular hardware or a software routine on a one-to-one basis. Therefore, in the present description, virtual circuit blocks (parts) having the functions of the embodiment are assumed to describe the embodiment. Moreover, the steps of each procedure in the present embodiment may change the execution order thereof, a plurality of the steps may be executed at the same time, or the steps may be executed by a different order in each execution as long as they are not against the nature thereof. Furthermore, all or part of the steps of each procedure of the present embodiment may be realized by hardware.

The present invention is not limited to the above described embodiment, and various changes, modifications, etc. can be made within the range in which the gist of the present invention is not changed.

What is claimed is:

1. An endoscopic device comprising:
an image sensor configured to acquire image data; and
a first processor comprising hardware, wherein the first processor is configured to:
  execute a first processing to process the image data, wherein the first processing involves a first processing load;
  acquire an instruction to perform a second processing to process the image data, wherein the second processing involves a second processing load different from the first processing load; and
  in response to acquiring the instruction, control a communication interface to output the image data to a second processor comprising hardware,
  wherein the second processor is provided separately from the endoscopic device, and
  wherein the second processor is configured to execute the second processing based on the image data,
wherein the first processor is configured to:
  receive priority information indicating a priority of generating at least a part of a live video based on the image data; and
  set the generating the at least a part of a live video based on the image data as one of the first processing and the second processing based on the priority information.

2. The endoscopic device according to claim 1,
wherein the second processing load is higher than the first processing load.

3. The endoscopic device according to claim 1,
wherein the first processing load is higher than the second processing load.

4. The endoscopic device according to claim 2,
wherein the first processing is display processing to process the image data to generate the at least a part of a live video, and
wherein the second processing is display processing to process the image data to generate a still image.

5. The endoscopic device according to claim 4,
wherein the first processing is display processing to process the image data to generate a still image.

6. The endoscopic device according to claim 4,
wherein the second processing is display processing to process the image data to generate a part of a live video.

7. The endoscopic device according to claim 1,
wherein the first processor is configured to:
  control a display to display a first image based on the first image information;
  control a storage to store the image signal; and
  in response to acquiring the instruction, control the endoscopic device-side communication interface to output the image data stored in the storage to the second processor.

8. The endoscopic device according to claim 7,
wherein the first processor is configured to acquire a recording instruction input through an input device as the instruction to perform the second processing.

9. The endoscopic device according to claim 7,
wherein the first processor is configured to acquire a freeze instruction input through an input device as the instruction to perform the second processing.

10. An endoscopic device comprising:
an image sensor configured to acquire image data; and
a first processor comprising hardware, wherein the first processor is configured to:
  execute a first processing to process the image data, wherein the first processing involves a first processing load;
  acquire an instruction to perform a second processing to process the image data, wherein the second processing involves a second processing load different from the first processing load; and
  in response to acquiring the instruction, control a communication interface to output the image data to a second processor comprising hardware,
  wherein the second processor is provided separately from the endoscopic device, and
  wherein the second processor is configured to execute the second processing based on the image data,
wherein the first processor is configured to:
  determine a throughput of each of the first processing and the second processing, and
  control the endoscopic device-side communication interface to output the image data stored in a storage based on the throughput of the second processor.

11. A system comprising:
the endoscopic device according to claim 1; and
the second processor.

12. A system comprising:
the endoscopic device according to claim 10; and
the second processor.

13. The system according to claim 11, further comprising a third processor comprising hardware;
wherein the first processor is configured to control the third processor-side communication interface to output the image signal data to the third processor, and
wherein the third processor is configured to:
  carry out control a third processor-side communication interface to output information to the endoscopic device; and
  a third processing to process the image data, wherein the third processing involves a third processing load.

14. The system according to claim 11,
wherein the first processor is configured to:
  determine the throughput of each of the first processing, the second processing, and the third processing;

control the endoscopic device-side communication interface to output the image data stored in the storage, based on the throughput to each of the second processor and the third processor; and synthesize the image data processed by the second processor and the image data processed by the third processor.

15. The system according to claim 11,
wherein the first processor is configured to:
  determine a distribution of processing load of each of the first processing, the second processing, and the third processing;
  control the endoscopic device-side communication interface to output the image data stored in the storage, based on the distribution of processing load to each of the second processor and the third processor; and
  synthesize the image data processed by the second processor and the image data processed by the third processor.

16. The system according to claim 12,
wherein the second processor is configured to:
  evaluate a processing capability of the second processor; and
  control the second processor-side communication interface to output a data of processing capability of the second processor to the first processor based on the processing capability;
wherein the third processor is configured to:
  evaluate a processing capability of the third processor; and
  control the third processor-side communication interface to output a data of processing capability of the third processor to the first processor, and
wherein the first processor is configured to determine the throughput of each of the second processor and the third processor based on the data of processing capability of the second processor and the data of processing capability of the third processor.

17. The system according to claim 13,
wherein the second processor is configured to:
  evaluate a processing capability of the second processor; and
  control the second processor-side communication interface to output data of performance of the second processor to the first processor based on the processing capability;
wherein the third processor is configured to:
  evaluate a processing capability of the third processor; and
  control the third processor-side communication interface to output data of processing capability of the third processor to the first processor, and
wherein the first processor is configured to determine a division load of each of the second processor and the third processor based on the data of processing capability of the second processor and the data of processing capability of the third processor.

18. A method comprising:
controlling an image sensor of an endoscopic device to capture image data;
executing, by a first processor comprising hardware of the endoscopic device, a first processing to process the image data, wherein the first processing involves a first processing load;
acquiring, by the first processor, an instruction to perform a second processing to process the image data, wherein the second processing involves a second processing load different from the first processing load; and
in response to acquiring the instruction, controlling, by the first processor, a communication interface to output the image data to a second processor comprising hardware,
wherein the second processor is provided separately from the endoscopic device,
wherein the second processor is configured to execute the second processing based on the image data, and
wherein the method further comprises:
  receiving, by the first processor, priority information indicating a priority of generating at least a part of a live video based on the image data; and
  setting, by the first processor, the generating the at least a part of a live video based on the image data as one of the first processing and the second processing based on the priority information.

* * * * *